United States Patent [19]

Cavalla et al.

[11] 4,428,954

[45] Jan. 31, 1984

[54] METHOD FOR TREATMENT OF CEREBROVASCULAR DISORDERS

[75] Inventors: John F. Cavalla, Isleworth; Michael G. Wyllie, Maidenhead, both of England

[73] Assignee: John Wyeth and Brother Limited, Maidenhead, England

[21] Appl. No.: 376,477

[22] Filed: May 10, 1982

Related U.S. Application Data

[63] Continuation of Ser. No. 250,963, Apr. 1, 1981, abandoned.

[30] Foreign Application Priority Data

Nov. 1, 1980 [GB] United Kingdom ............... 803203

[51] Int. Cl.³ .......................................... A61U 31/44
[52] U.S. Cl. ................................................. 424/263
[58] Field of Search ....................................... 424/263

[56] References Cited

U.S. PATENT DOCUMENTS 3,527,761 9/1970 Archibald ........................ 424/267

FOREIGN PATENT DOCUMENTS 1218570 1/1971 United Kingdom .

OTHER PUBLICATIONS

Paciorek & Wyllie, Brit. J. Pharm., vol. 70, 1980, pp. 92P–93P.

*Primary Examiner*—Stanley J. Friedman
*Attorney, Agent, or Firm*—George Tarnowski

[57] ABSTRACT

Treating cerebrovascular disorders characterized by poor oxygenation with 3-[2-C benzamide-1-piperidyl) ethyl] indole.

2 Claims, No Drawings

METHOD FOR TREATMENT OF CEREBROVASCULAR DISORDERS

This is a continuation of application Ser. No. 250,963 filed Apr. 1, 1981.

This invention relates to a novel method of treatment, more particularly to a method for improving mental performance in animals with cerebrovascular disorders characterised by poor oxygenation.

In U.K. patent specification No. 1,218,570 there are described and claimed a class of indole derivatives which have various pharmacological activities, especially action on the cardiovascular system. One of these compounds, 3-[2-(4-benzamido-1-piperidyl)ethyl]indole has demonstrated valuable antihypertensive properties in human beings in clinical trials. This compound has the internationally approved name: indoramin.

We have now found that indoramin behaves in a similar manner to two drugs, naftidrofuryl oxalate and dihydroergotoxine mesylate, both widely used in the treatment of cerebrovascular disorders characterised by poor oxygenation. More particularly we have found that indoramin, naftidrofuryl oxalate and dihydroergotoxine mesylate are able to delay the expected drop in adenosinetriphosphate (ATP) level in the cerebral cortex of rats when exposed to hypoxic conditions (i.e. 4% $O_2$, 0.05% $CO_2$ and 95.95% $N_2$). Results show that indoramin promotes synthesis of ATP in the rat cerebral cortex tending to maintain 'normal' ATP levels under hypoxic conditions.

It is known that the amount of ATP present is a regulating factor on the activity of one of the most important enzymes controlling central nervous system excitability, viz. sodium, potassium activated, magnesium-dependent adenosine triphosphatase ($Na^+,K^+$-ATPase). $Na^+,K^+$-ATPase is involved in maintenance of resting membrane potential and neurotransmitter release and inhibition of this enzyme can result in pronounced behavioural effects. Normally because of adequate synthesis the levels of ATP are rarely limiting, any imbalance being quickly restored. The effect of a drug is therefore only apparent where an adverse condition such as hypoxia dramatically alters the ATP level. Under certain stress or age-dependent conditions cellular ATP synthesis may be impaired. The ability to redress any imbalance in ATP level by promoting ATP synthesis is potentially very useful in the treatment of cerebrovascular disorders charcterised by poor oxygenation, especially mild to moderate impairment of mental function in the elderly.

Accordingly this invention provides a method for the treatment or prevention of cerebrovascular disorders characterised by poor oxygenation in an animal which comprises administering to said animal a therapeutically effective amount of 3-[2-(4-benzamido-1-piperidyl)ethyl]indole (indoramin) or a pharmaceutically acceptable acid addition or quaternary ammonium salt thereof.

The following test procedure was used to test indoramin, naftidrofuryl oxalate and dihydroergotoxine mesylate on ATP levels in hypoxic rats.

Rats were exposed either to air or to a special gas mixture (4% $O_2$, 0.05% $CO_2$, 95.95% $N_2$) for 5 minutes. The animals were then decapitated and the cortices removed and placed in 2 ml of 0.1 N perchloric acid in methanol, on dry ice (0° C.). The extracted ATP was assayed either by comparing the inorganic phosphate release by purified adenosinetriphosphatase (EC 3613) with that released from ATP standards or fluorimetrically as described by J. R. Williamson and B. Crokey in Methods of Enzymology, Vol. 13 p434, Academic Press, New York, 1969 (Ed. J. Lowenstein). Drugs were administered orally in a 0.5% hydroxypropyl-methyl-cellulose/0.9% saline vehicle (2 ml/kg) 2 hours before the animals were killed.

The effect of test drugs on brain ATP levels in groups of 6–12 rats are shown below:

| Drug | Dose (mg/kg po) | ATP concentration ($\mu$mol/o cortex ± S.E.M.) Normal | Hypoxia |
|---|---|---|---|
| Vehicle |  | 2.6 ± 0.04 | 1.6 ± 0.02 |
| Indoramin | 3 | 2.6 ± 0.1 | 2.4 ± 0.03 |
|  | 1 |  | 2.3 ± 0.02 |
|  | 0.3 |  | 1.8 ± 0.03 |
| Dihydroergotoxine mesylate | 3 | 2.6 ± 0.07 | 2.4 ± 0.04 |
|  | 1 |  | 2.4 ± 0.03 |
|  | 0.3 |  | 1.9 ± 0.02 |
| Naftidrofuryl oxalate | 100 | 2.6 ± 0.05 | 2.4 ± 0.07 |
|  | 10 |  | 1.9 ± 0.02 |
|  | 1 |  | 1.5 ± 0.04 |

These results show that indoramin behaved like the two cerebral activators by protecting ATP levels in the hypoxic state when administered in sufficient amount.

In a separate experiment the rate of ATP synthesis in rat cerebral cortex slices was measured manometrically (see D. J. K. Balfour and J. C. Gilbert, Biochem. Pharmac., 20, 1151 (1971) in a Krebs-phosphate medium. For control rats under hypoxic conditions the rate of production was 52 $\mu$mol ATP/g. cortex/hour whereas for indoramin treated rats the rate increased to 92 $\mu$mol ATP/g. cortex/hour. Thus not only does indoramin mimic the effect of the two known cerebral activators on ATP level in the hypoxic state but it also has the advantage of acting directly to promote the rate of ATP synthesis under hypoxic conditions.

Other antihypertensive agents such as clonidine and phentolamine have been tested in the procedures above and found to have little or no effect relative to control.

When used in the method of this invention, indoramin or a pharmaceutically acceptable acid addition or quaternary ammonium salt thereof may be administered alone or in the form of a pharmaceutically acceptable composition. Suitable carriers are well known in the art. The particular dosage will depend on the chosen route of administration and standard pharmaceutical practice. Preferably the composition is in unit dosage form, e.g. tablets or capsules.

Based on the animal experiments above, indoramin is of comparable activity to dihydroergotoxine mesylate and accordingly a dose regimen of about 1 to 90 mgs/day may be used for treating humans suffering from cerebrovascular disorders.

We claim:

1. A method for the treatment of cerebrovascular disorders characterised by poor oxygenation in an animal afflicted with such a disorder which comprises administering to said animal a therapeutically effective amount of 3-[2-(4-benzamido-1-piperidyl)ethyl]indole or a pharmaceutically acceptable salt thereof.

2. A method for the treatment of impairment of mental function in the elderly which comprises administering to a person so afflicted a therapeutically effective amount of 3-[2-(4-benzamido-1-piperidyl)ethyl]indole or a pharmaceutically acceptable salt thereof.

* * * * *